United States Patent [19]

Frankel

[11] Patent Number: 4,825,858
[45] Date of Patent: * May 2, 1989

[54] AUTOMATIC INTUBATION DEVICE FOR GUIDING ENDOTRACHEAL TUBE INTO TRACHEA

[76] Inventor: Alfred R. Frankel, 403 Gulf Way - Apt. 701, Pass-A-Grille Beach, Fla. 33706

[ * ] Notice: The portion of the term of this patent subsequent to Jun. 16, 2004 has been disclaimed.

[21] Appl. No.: 22,790

[22] Filed: Mar. 6, 1987

Related U.S. Application Data

[63] Continuation-in-part of Ser. No. 820,664, Jan. 20, 1986, Pat. No. 4,672,960, Continuation-in-part of Ser. No. 640,843, Aug. 15, 1984, abandoned.

[51] Int. Cl.[4] ............................................. A61M 16/00
[52] U.S. Cl. ......................... 128/200.26; 128/207.14; 128/207.15
[58] Field of Search .................... 128/200.26, 207.14, 128/207.15, DIG. 26; 604/160, 171, 280, 281, 282, 283, 284, 164; 138/111, 115, 116, 117

[56] References Cited

U.S. PATENT DOCUMENTS 4,023,596  5/1977  Tate ..................................... 138/111
4,454,887  6/1984  Kruger .......................... 128/207.14
4,672,960  6/1987  Frankel ......................... 128/200.26

Primary Examiner—Edward M. Coven
Assistant Examiner—K. M. Reichle
Attorney, Agent, or Firm—Walter J. Monacelli

[57] ABSTRACT

The automatic intubation device described herein consists of an endotracheal tube which can be inserted automatically into the trachea without the use of a laryngoscope or a physician skilled in its use and which will avoid obstruction on the way to the trachea and comprises a combination of: (1) a flexible guide having no more than a slight curvature in the length thereof and having a male adaptor or track running at least a substantial portion of its length and (2) the endotracheal tube to be inserted into the trachea which endotracheal tube may have a substantial amount of curvature therein and also has a slit extending from the advance or distal end of the endotracheal tube, extending longitudinally for a short distance along said tube and designed to fit onto the adaptor of the guide. The guide is introduced through the mouth and pharynx to the esophagus and the endotracheal tube is guided by sliding on the adaptor of the guide to where it leaves this adaptor beyond the epiglottus and at or before reaching the entrance to the esophagus at which point curvature of the endotracheal tube bends it toward and into the trachea.

17 Claims, 3 Drawing Sheets

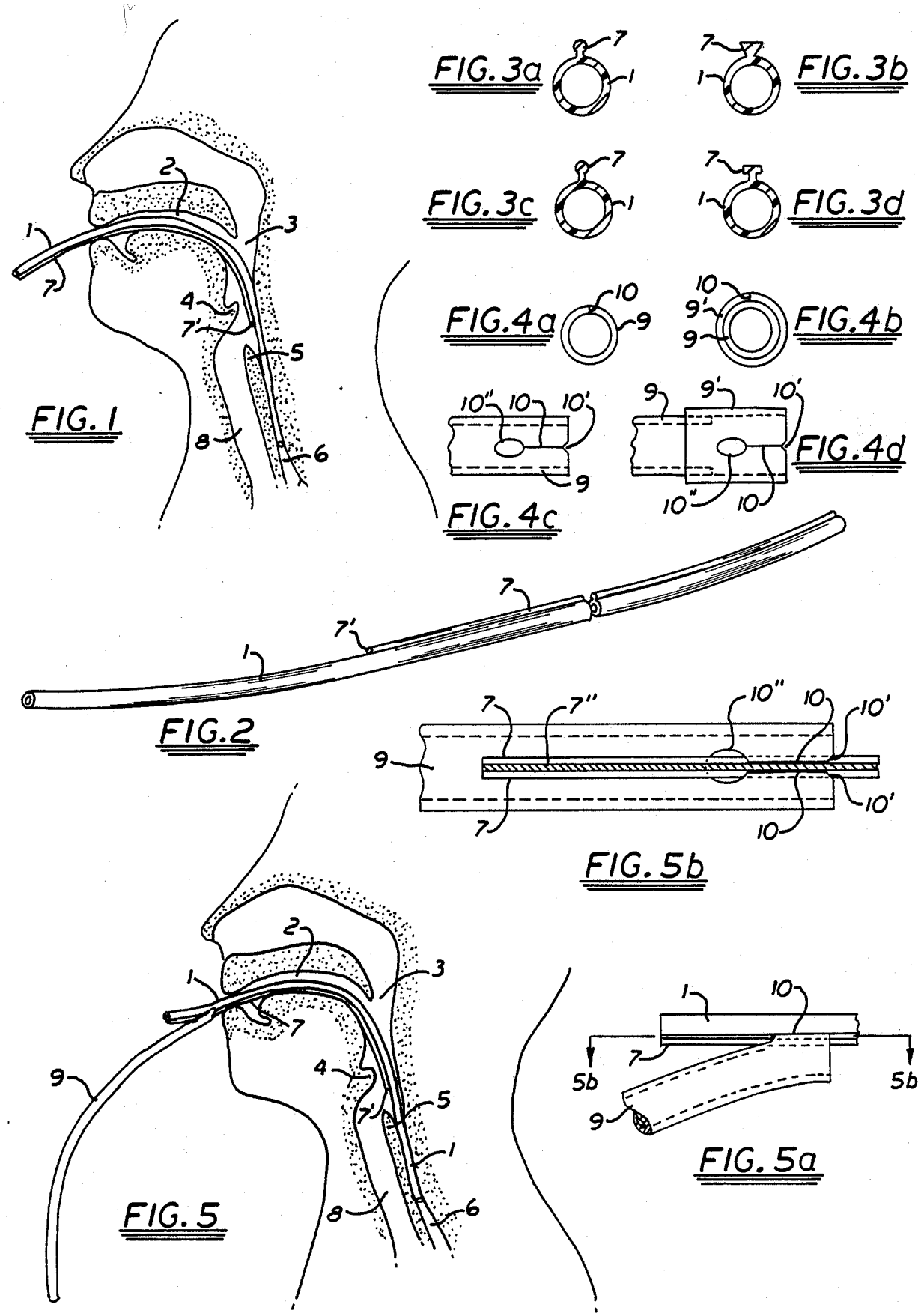

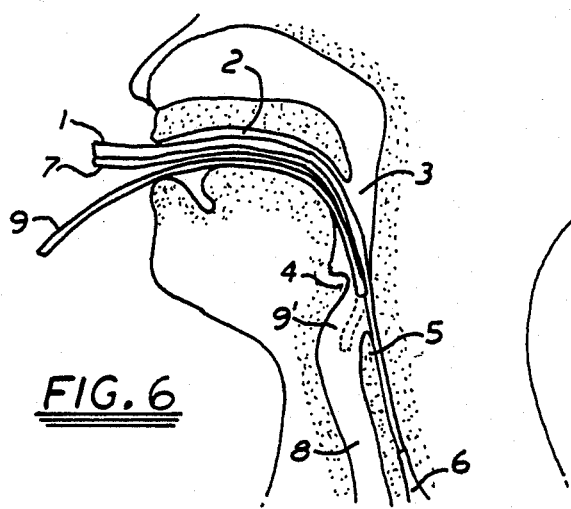
FIG. 6
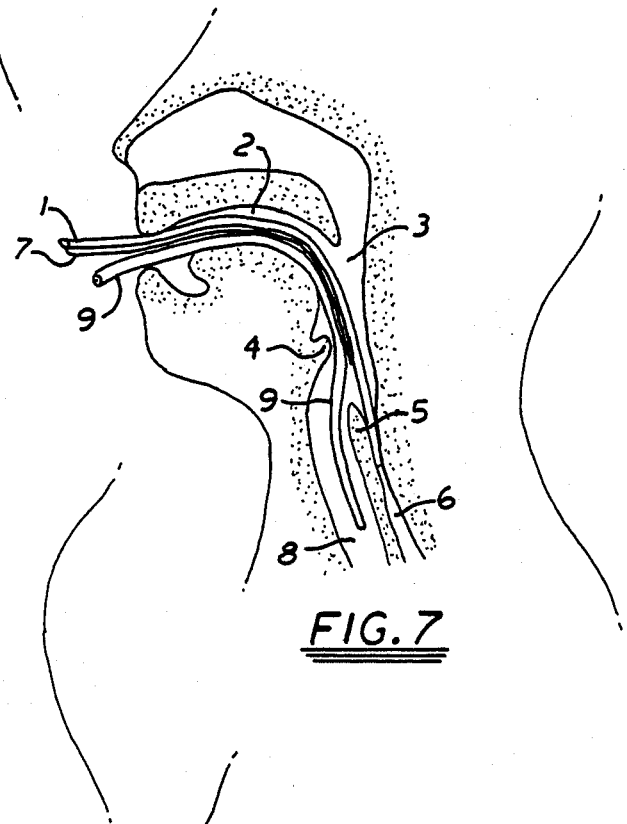
FIG. 7
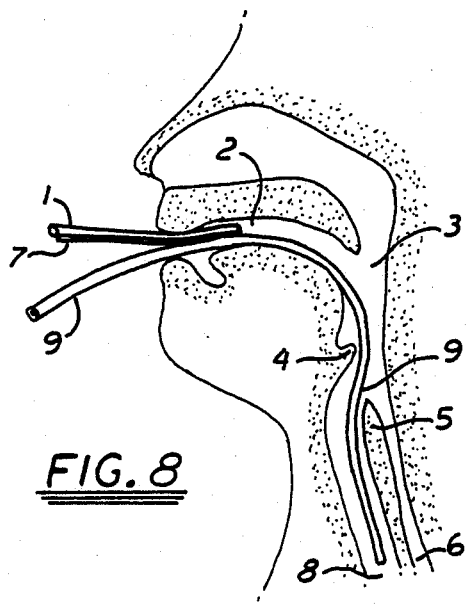
FIG. 8
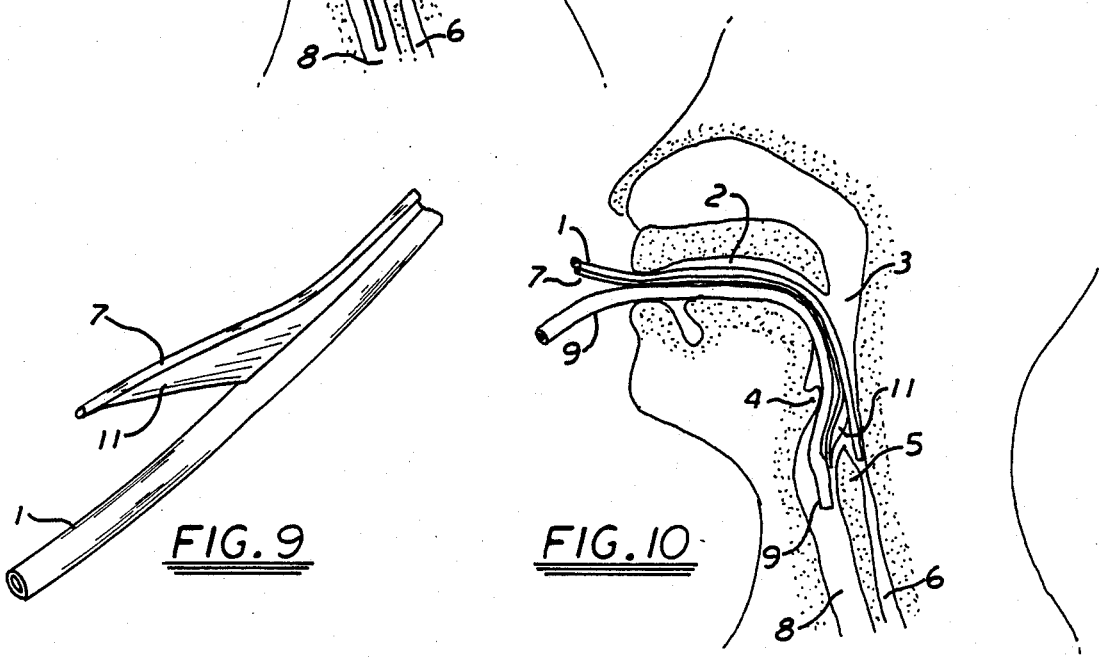
FIG. 9
FIG. 10

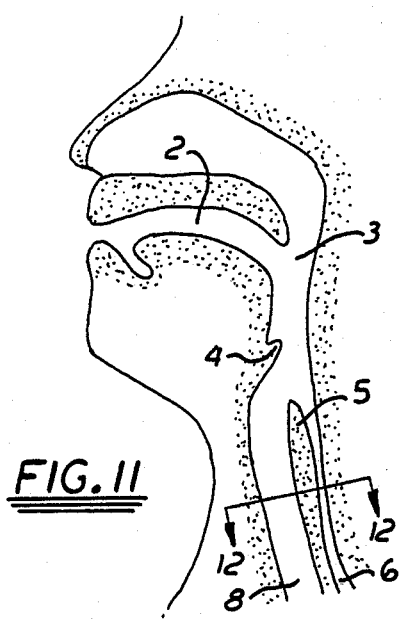
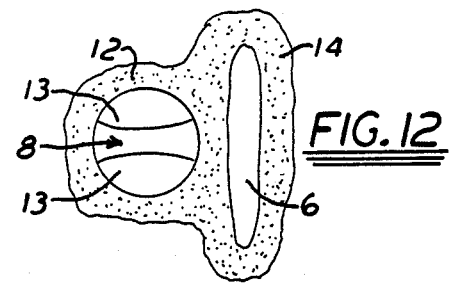
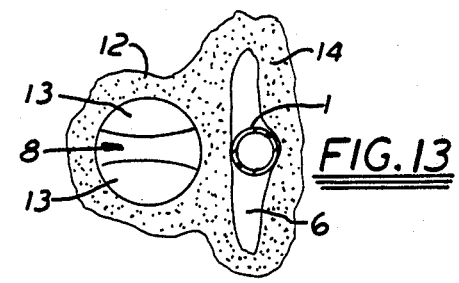
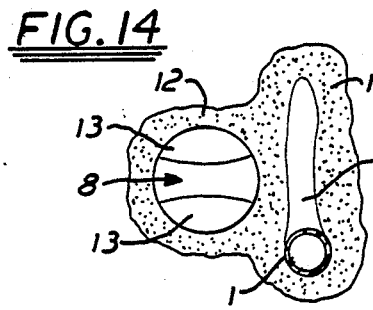
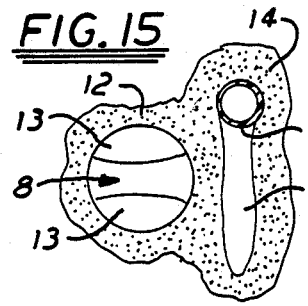
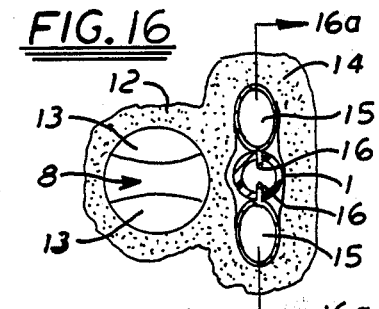
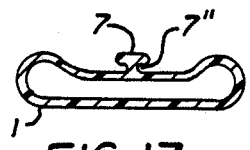
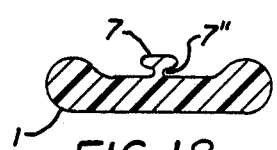
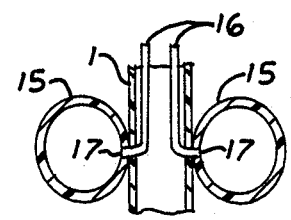
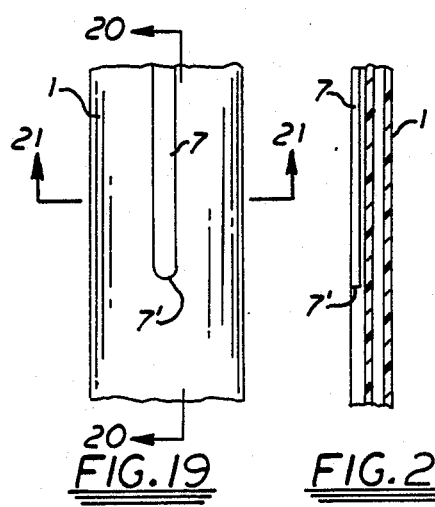
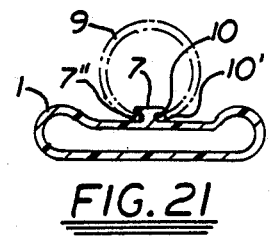
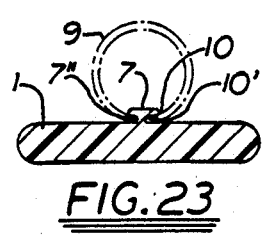
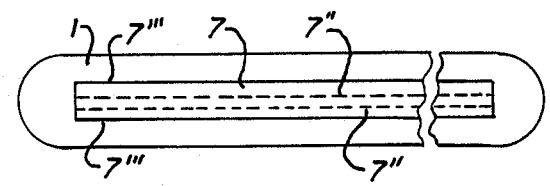
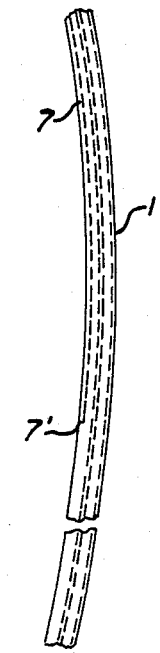

AUTOMATIC INTUBATION DEVICE FOR GUIDING ENDOTRACHEAL TUBE INTO TRACHEA

This application is a continuation-in-part of application Ser. No. 06/820,664 filed Jan. 21, 1986, now U.S. Pat. No. 4,672,960, which in turn is a continuation-in-part of application Ser. No. 05/640,843 filed Aug. 15, 1984 now abandoned.

BACKGROUND OF THE INVENTION

1. Field of the Invention

This invention relates to a device for guiding an endotracheal tube into the trachea without the use of a laryngoscope. More specifically it relates to an esophageal guide adaptor or track to serve in directing the endotracheal tube into the trachea. Still more specifically it relates to an esophageal guide having a male adaptor running along a substantial portion of the length thereof and adapted to be fitted by a slit on the advance or distal end of the endotracheal tube running longitudinally for a short distance on the endotracheal tube.

2. Description of the Prior Art

Endotracheal tubes are used to provide relief for patients requiring artificial ventilation. These tubes are presently inserted by a skilled physician using a laryngoscope to displace the epiglottus and allow the physician operator to directly visualize the trachea and the vocal chords and under direct vision insert the endotracheal tube.

Attempts to blindly pass an endotracheal tube will, because of anatomical consideration, generally result in the tube being passed into the esophagus. This principle is used currently in the blind passage of esophageal airways which work by obstructing the esophagus with an inflated balloon. Then with air forced into the mouth and into the upper airway but not able to flow past the obstructing balloon in the esophagus, the air is forced into the trachea and to the lungs. However, an endotracheal tube introduced into the trachea will provide oxygen directly to the lungs and thereby is more efficient.

Applicant's pending U.S. application Ser. No. 820,664 filed Jan. 20, 1986, describes an automatic intubation device comprising (1) a flexible guide having no more than slight curvature in the length thereof and having a male or female adaptor running at least a substantial portion of the length thereof and (2) an endotracheal tube to be inserted into the trachea which endotracheal may have a substantial amount of curvature therein and also has a female or male adaptor or track complementary to the adaptor on the guide and designed to fit onto the adaptor of the guide.

The guide is introduced through the mouth and pharynx to the esophagus and the endotracheal tube is guided by sliding on the adaptor of the guide to where it leaves this adaptor beyond the epiglottus and at or before reaching the entrance to the esophagus at which point curvature of the endotracheal tube bends it toward and into the trachea or where the esophagus is substantially filled or blocked by the guide the endotracheal tube is turned by the dividing wall toward the trachea.

OBJECTIVES OF THE INVENTION

It is an objective of this invention to design a simple device which will permit the blind insertion of an endotracheal tube directly into the trachea by medical professionals unskilled in the use of direct laryngoscopy for the emergency insertion of endotracheal tubes.

It is also an objective of this invention to design a simple device consisting of an esophageal guide and a partially slit endotracheal tube which will permit the blind placement of the endotracheal tube past the epiglottus, allow the endotracheal tube to be maintained in the midline and allow it to disengage itself from the esophageal guide and move anteriorly to enter the trachea.

It is also an objective to use the easy passage of the esophageal tube to assist in the passage of the endotracheal tube past the epiglottus.

Additional objectives will be obvious from the description of the invention.

SUMMARY OF THE INVENTION

In accordance with the present invention it has been found that the passage of an endotracheal tube can be guided easily and simply through the pharynx and into the trachea by inserting first an esophageal guide comprising either a tube or solid rod having a male adaptor or track running along the outside of the esophageal guide and at least a substantial portion of the length of the esophageal guide and then introducing an endotracheal tube alongside the esophageal guide, this endotracheal tube having a slit at the distal end thereof extending longitudinally for a short distance and adapted to being fitted to the male adaptor or track fixed to the esophageal guide so that the guide will serve to guide the endotracheal tube as the latter is advanced toward the trachea. For example, the esophageal guide has a male adaptor running longitudinally on the exterior thereof and the slit on the endotracheal tube will fit onto the male adaptor of the esophageal guide. As the endotracheal tube is advanced through the mouth, through the pharynx and toward the trachea, the slit portion thereof will slide on the adaptor portion of the esophageal guide and be guided thereby.

The adaptor portion on the esophageal guide is of an appropriate length so that it will be advance beyond the epiglottus and possibly beyond the dividing or separating wall between the trachea and the esophagus. With the space of the esophageal opening occupied by the guide, the advancement of the endotracheal tube will terminate at the dividing wall separating the esophagus and the trachea, after which the guide is withdrawn. When the terminus of the adaptor is withdrawn past this dividing wall, the endotracheal tube will slide off the terminus of the adaptor on the esophageal guide and the linear curvature of the endotracheal tube will turn this tube away from the esophagus and toward the trachea. Further advancement of the endotracheal tube assures entry of this tube into the trachea without having encountered or having been blocked by the epiglottus, and by maintaining the endotracheal tube in the midline the endotracheal tube will be allowed to move anteriorly.

For the esophageal guide the adaptor affixed thereto is positioned on the inner side of whatever linear curvature is present. With the endotracheal tube the slit at the distal end is on the outer side of the linear curvature present therein. This arrangement insures that as the endotracheal tube is released from the adaptor on the esophageal guide its linear curvature will turn it toward the opening of the tracheal tube.

The position of the distal end of the esophageal guide can be determined or judged by the length of the portion introduced. In this way it is possible to determine the position of that part of the esophageal tube at which the attached adaptor is terminated. As stated previously this terminal of the adaptor is advantageously positioned beyond the epiglottus and below the corniculate cartilage and the arytenoid muscle and cartilage which comprise the separating wall between the trachea and the esophagus. In a particular modification described hereinafter this terminal of the adaptor on the esophageal tube can have a protruding shape which will hook onto or be blocked by this dividing wall. This provides an exact determination of the positioning of this terminal and may also be used to assist in the projection of the endotracheal tube toward the trachea.

Once the distal end of the endotracheal tube has entered the trachea the esophageal guide tube can be withdrawn while or even after the endotracheal tube is further advanced into the trachea.

While it is preferred to have the adaptor or track end at a point short of the distal end of the guide, it is possible also to have the track run all the way to the distal end. In such case the operator may depend on blockage of the endotracheal tube by the dividing wall and rely on the withdrawal of the guide to release the endotracheal tube near the entrance to the trachea.

A preferred modification of this invention is one in which the esophageal tube has an oblong or flat cross-section so that it will more truly fit the shape of the esophagus. With the esophageal guide conforming more truly to the cross-section of the esophagus, a track or adaptor positioned in the middle of one of the longer sides of the oblong will position the endotracheal tube which rides on the track more exactly in a middle position to enter the trachea as described more fully hereinafter.

The end of the slit remote from the distal end of the endotracheal tube advantageously communicates with an opening in the wall of the said tube which facilitates the sliding of the slit on the track on the guide. Otherwise a sharp angle turn or bending of the endotracheal tube is required at the point where the portion of the tube beyond the slit bends away from the track.

SPECIFIC EMBODIMENTS OF THE INVENTION

The device of this invention may be illustrated by reference to the accompanying drawings in which:

FIG. 1 is a side elevational view showing various passageways in a patient's head with a modification of the esophageal guide extending through the pharynx and into the esophagus.

FIG. 2 is a side elevational view of an esophageal guide only slightly curved with a male adaptor affixed to and extending along a substantial portion of its length.

FIGS. 3a through 3d show cross-sections of esophageal guides with various modifications of male adaptors attached to the exterior thereof.

FIG. 4a is an end view of the distal end of an endotracheal tube showing the slit.

FIG. 4b is an end view of the distal end of an endotracheal tube over which a sleeve has been affixed having a slit therein.

FIG. 4c is a side elevational view of the distal end portion of the endotracheal tube of FIG. 4a showing the slit in the tube.

FIG. 4d is a side elevational view of the distal end portion of the endotracheal tube and sleeve as shown in FIG. 4b.

FIG. 5 is a side elevational view showing various passageways in a patient's head with the esophageal guide extending through the pharynx and into the esophagus as shown in FIG. 1 but also having an endotracheal tube about to be introduced into the mouth.

FIG. 5a is an enlarged side elevational view of the end of the guide still outside the mouth and of the distal end of the endotracheal tube with the slit fitted onto the male adaptor of the guide.

FIG. 5b is a longitudinal cross-sectional view taken at line 5b—5b of FIG. 5a.

FIG. 6 shows the same view as shown in FIG. 5 with the endotracheal tube advanced further through the mouth and the pharynx with the slit of the endotracheal tube fitted onto the male adaptor of the esophageal guide.

FIG. 7 shows the same view as shown in FIG. 6 with the distal end of the endotracheal tube separated from the esophageal guide and extending into the trachea.

FIG. 8 shows the same view as in FIG. 7 with the distal end of the endotracheal tube extended further into the trachea and the esophageal guide substantially all withdrawn from the mouth.

FIG. 9 shows a perspective view of an end portion of an esophageal guide which has a tracheal hook and skid extending away from the esophageal tube.

FIG. 10 shows a similar view as in FIG. 7 except that the esophageal guide has a male adaptor with the tracheal hook and skid of FIG. 9.

FIG. 11 is a side elevational view showing the various passageways in a patient's head as shown in FIGS. 1, 5–9 and 10 but without the various tubes.

FIG. 12 is a cross-sectional view of the trachea and esophagus taken at line 12—12 of FIG. 11.

FIG. 13 is a cross-sectional view similar to that of FIG. 12 except that an esophageal guide has been inserted in the preferred position directly opposite to the trachea.

FIGS. 14 and 15 are cross-sectional views similar to that of FIG. 13 except that the inserted esophageal guide is positioned to one side or the other of the trachea.

FIG. 16 is a cross-sectional view similar to that of FIG. 13 in which the inserted esophageal guide has a balloon expanded on each side thereof to insure location of the esophageal guide centrally and directly opposite the trachea.

FIG. 16A is a cross-sectional view taken at line 16A—16A of FIG. 16.

FIG. 17 is a cross-sectional view of an esophageal guide having an oblong cross-section conforming to the interior of the esophagus and having a male adaptor or track extending along a portion of the tube.

FIG. 18 is a cross-sectional view similar to that of FIG. 17 except that the esophageal guide has a solid oblong cross-section.

FIG. 19 is an elevational front view of a broken section of the oblong tube shown in FIG. 17 with a track or adaptor extending in the middle of the exterior and partway down the length of the oblong tube.

FIG. 20 is a side elevational view of the broken section of FIG. 19 take at line 20—20.

FIG. 21 is a cross-sectional view of FIG. 19 taken at line 21—21 of FIG. 19 with a cross-sectional view of an endotracheal tube of the type shown in FIGS. 4a and 4c.

FIG. 22 is a top linear view of the combined guide and endotracheal tube shown in the cross-sectional view of FIG. 23.

FIG. 23 is a cross-sectional view similar to that of FIG. 21 except that the esophageal guide is flat and has a solid oblong cross-section.

FIG. 24 is a side view of the esophageal tube 1 showing a slight curvature through its length.

In FIG. 1 the flexible esophageal guide 1, no more than slightly curved along its length, is inserted in the patient's mouth 2 and pharynx 3 past the epiglottus 4. The corniculus or dividing wall 5 comprises the corniculate cartilage and the arytenoid cartilage which separates the trachea from the esophagus. The esophageal guide has a male adaptor 7 affixed thereto and extending along a substantial portion of the length thereof with the terminus 7' positioned near the opening of the trachea 8.

FIG. 2 is a perspective view of an esophageal guide 1 of this invention with male adaptor 7 affixed thereto and extending a substantial portion of the length thereof with terminus 7'.

FIGS. 3a through 3d show cross-sections of several modifications of esophageal guides with male adaptors 7 of various shapes affixed thereto.

FIG. 4a is an end view of the distal end of the endotracheal tube 9 showing slit 10.

FIG. 4c shows a longitudinal view of the end portion of endotracheal tube 9 having a slit 10 at the distal end. The end 10' of slit 10 is preferably rounded or curved to avoid a sharp corner or edge which might tear the wall of a passageway. Opening 10" may be omitted but is advantageously provided to allow a gradual transition of the position of having the slit 10 fitted on the male adaptor 7 of guide 1 to the position where the endotracheal tube is separated from the guide.

FIG. 4b shows sleeve 9' affixed over the distal end of endotracheal tube 9 with slit 10 in the sleeve.

FIG. 4d is a longitudinal top view of sleeve 9' fitted over the distal end portion of endotracheal tube 9 showing slit 10, opening 10" and rounded or curved edges 10' of slit 10. As stated above these rounded or curved edges are to avoid any tearing or cutting of the walls of the human passageways through which the endotracheal tube is passed.

FIG. 5 is a view similar to that of FIG. 1 with endotracheal tube 9, which is advantageously more curved along its length than the esophageal guide and being affixed to the esophageal guide in a preliminary position with the slit of the endotracheal tube being fitted over the track or adaptor 7 on the esophageal guide 1. The distal end 7' of the track is positioned just short of the esophagus with the distal end of the esophageal tube extending into the esophagus.

FIG. 5a is a partial view of the end of esophageal guide 1 which remains outside the mouth with the slit 10 of the endotracheal tube being introduced on the track 7 on the guide.

FIG. 5b is a longitudinal partial cross-sectional view taken at line 5b—5b of FIG. 5a showing the narrow part 7" of adaptor 7 embraced by the two edges of slit 10. Opening 10" is at the end of slit 10 through which track 7 separates from the slit 10 where endotracheal tube 9 is no longer attached to the track 7 of esophageal guide 1.

FIG. 6 is a view similar to that of FIG. 5 with the endotracheal tube 9 extended all the way to the end of adaptor 7 (not shown). When the endotracheal tube is advanced to the position shown by the dotted lines 9', the curvature of the endotracheal tube turns its distal end away from the esophageal guide and into the trachea as shown in FIG. 7.

FIG. 8 is a view similar to that shown in FIG. 7 except that the esophageal guide has been substantially withdrawn.

FIG. 9 shows a special modification of an esophageal guide of this invention with the male adaptor 7 veering sharply away from its substantially parallel attachment to the esophageal guide. This sharp veering is effected by means of fin 11 which is increased in width toward the end of adaptor 7. This fin decreases sharply in supporting width from its greatest width at the adaptor terminus to a zero width a short distance from the terminus. The fin is cut at an angle so as to form a hook as shown in FIG. 9 which will position the end of adaptor 7 far enough away from the esophageal guide to be positioned at the entrance to the trachea. This positioning gives even greater assurance that the endotracheal tube 9 will be guided directly into the trachea as shown by the view of FIG. 10.

FIG. 11 is a side elevational view showing passageways in a patient's head as shown in FIG. 1 except that the tubes shown in FIG. 1 are omitted. FIG. 12 shows a cross-sectional view of the esophagus 6 and of the trachea 8 taken at line 12—12 of FIG. 11. The esophagus 6 has an oblong cross-section with esophageal wall 14. The trachea 8 has cartilogenrus ring 12 and two vocal chords 13.

In a preferred modification of the invention the esophageal guide has an oblong or flat outer configuration. The esophagus has a cross-section as shown in FIG. 12 where the relative positioning of the trachea and the esophagus is shown. FIG. 13 shows the preferred position of the esophageal guide when it is inserted for the purposes of this invention. In this way the esophageal guide is directly opposite the trachea and the track or adaptor on which the endotracheal tube is guided will locate the endotracheal tube in appropriate position to enter the trachea. FIGS. 14 and 15 show how the esophageal guide may be positioned to one side or the other of the trachea which is undesirable for locating the endotracheal tube for entrance into the trachea. In order to insure that the esophageal guide 1 is located properly as shown in FIG. 13, the esophageal guide 1 may have ballons 15 positioned on each side of the esophageal guide, as shown so that when the end 7' of adaptor or track 7 is positioned between the epiglottus 4 and the wall 5 dividing the trachea from the esophagus the balloons may be inflated as shown in FIG. 16, so that regardless of the location of esophageal guide 1 in the esophagus the balloons will move tube 1 to a center position opposite the trachea so that when the endotracheal tube 9 leaves track or male adaptor 7, it will be positioned to enter the trachea 8. The cross-sectional view of FIG. 16A shows two small tubes inside esophageal guide 1 leading to openings 17 connecting with the interior of balloons 15. The small tubes 16 may be joined to each other above their connections to the balloons and the joined tube connected to a compressed air source, or the two individual tubes may be each connected to a compressed air source such as a compressed air cylinder.

FIG. 17 shows a cross-sectional view of a preferred oblong shaped esophageal guide 1 with track or male adaptor 7. FIG. 18 shows a similar cross-sectional view of a solid tube of similar oblong configuration.

FIGS. 19 and 20 show front and side elevational views respectfully of a broken section of the tube shown in FIG. 17. The terminus 7' of track 7 is positioned away from the lower end of tube 1 so that it may be positioned appropriately as described above with respect to FIGS. 5 and 13. With this structure the endotracheal tube coming off the end 7' of track 7 will be automatically properly centered for entrance into the trachea 8.

FIG. 21 shows a cross-section of the oblong type of esophageal guide 1 shown in FIG. 19 and 20 with an endotracheal tube 9 in phantom positioned with its slit 10 embracing the male adaptor or track 7 affixed to esophageal guide 1.

FIG. 22 shows a bottom longitudinal view of the guide 1 having a flat oblong cross-section as shown in FIG. 23. Track or adaptor 7 is shown on the viewer's side and the narrow neck of the adaptor is shown by dotted lines 7'' and the wider portion of the adaptor shown as 7'''.

FIG. 23 shows in phantom the edges of slit 10 in endotracheal tube 9 embracing the narrow neck 7'' of adaptor or track 7 attached to guide 1 as shown in FIG. 22.

FIG. 24 is a side view of the esophageal guide 1 (not according to scale) as shown in FIGS. 17 and 21 showing the slight curvature in the length of tube. Dotted lines shown the track 7 hidden within the interior curvature of the width of tube as illustrated in the views of FIGS. 19 and 20.

In FIGS. 17-23, the various tubes are shown in exagerated size in order to depict more clearly the details of these tubes. Actually the tubes described above advantageously have in the oblong cross-section a width of ½ to 1½ inches and 1/16 to ½ inches in thickness or may be smaller or slightly larger so long as they are capable of passing without difficulty through the various passageways to be maneuvered. They may be made of materials similar to those presently used for these purposes, for example, polyethylene, polypropylene and other flexible plastic materials that will not irritate in any way the tissues with which they come in contact.

The manner of using and manipulating the esophageal guide and endotracheal tube are made clear from the above descriptions. It is important however, that the esophageal guide should be introduced and maintained with the adaptor on the inner side of the linear curvature of the tube so that as the endotracheal is released therefrom it will be in the appropriate position to bend toward the trachea.

While it is preferred that the slit attached to or incorporated in the endotracheal tube extends for a short portion of the length of the endotracheal tube, it is also possible to have this slit extend all the way or for only a relatively short distance from the distal end of the endotracheal tube. The purpose of this slit is to guide the distal end of the endotracheal tube to or near the dividing wall between the esophagus and the trachea after which the curvature of the endotracheal tube will effect a turn of the distal end toward the opening of the trachea.

While reference has been made above to the desirability of locating the terminus 7' of track 7 near the opening of the trachea so that the endotracheal tube as it comes off the track will, by nature of its greater curvture, turn toward the trachea, it is also possible where the distal end of the endotracheal tube can be made to strike the upper edge of the corniculus 5 (the wall separating the trachea from the esophagus) such as by the device shown in FIG. 9 or by having the size and shape of the esophageal tube sufficient to fill the esophagus, it will not be necessary to locate the terminus 7' of track 7. Where the endotracheal tube can be made to strike the upper edge of wall 5, the track 7 can extend down into the esophagus and as the esophageal tube is withdrawn, with the endotracheal tube held in position, the endotracheal tube will be released by the withdrawal of the esophageal tube and will be allowed by its curvature to turn toward the trachea.

While it may be preferred to have curvature in the endotracheal tube as described above to insure the turning of the end thereof as it leaves the distal end of the adaptor or track on the guide, it is also possible to use a flexible endotracheal tube that has little or no linear curvature and instead depend on the circumstance of having the esophagus substantially blocked or filled with the esophageal guide. In such case when the terminus of the adaptor on the guide is positioned or withdrawn to a point just outside the entrance to the esophagus, further advancement of the distal end of the endotracheal tube will result in having the dividing wall shunt the said distal end of the endotracheal tube toward the trachea.

While certain features of this invention have been described in detail with respect to various embodiments thereof, it will of couse be apparent that other modifications can be made within the spirit and scope of this invention, and it is not intended to limit the invention to the exact details shown above except insofar as they are defined in the following claims.

I claim:

1. A device for facilitating the insertion of an endotracheal tube into a patient's trachea comprising:
   (a) a flexible guide having a distal end, having no more than slight linear curvature along its length, having a size and length appropriate for insertion through the patient's mouth and pharynx and for at least the distal end thereof to fit into the patient's esophagus and having a male adaptor extending along a substantial portion of the length thereof and having a terminus;
   (b) an endotracheal tube comprising a flexible tube having greater linear curvature along its length than that of said guide, having a size and length appropriate for insertion through the patient's mouth and pharynx into the patient's trachea and having a distal end and a longitudinal slit starting at the distal end and extending a short distance along a portion of the length thereof, said slit being capable of fitting onto and embracing the said adaptor on said guide so as to be slidably mounted thereon, the said guide and tube being connected for use by having a portion of the said male adaptor embraced by said slit of said endotracheal tube.

2. The device of claim 1, in which the said adaptor on said guide is on the inner side of any linear curvature therein and the said slit on said endotracheal tube is on the outer side of the linear curvature thereof.

3. The device of claim 2, in which the edges of the end of the slit remote from the distal end of said endotracheal tube being spaced apart from one another a greater distance than the edges of the remainder of the slit and thereby defining an opening.

4. The device of claim 3, in which the said adaptor on said guide has its terminus positioned at least a short distance from the distal end of said guide.

5. The device of claim 4, in which the terminus of the said adaptor of said guide is laterally spaced a substantial distance from said guide and said guide further including a fin attaching the terminus to the guide and the dimension of the fin extending between the adaptor and the guide decreasing sharply from a maximum at said terminus to zero width a short distance from the terminus in a direction away from the distal end of the guide.

6. The device of claim 1 in which said guide has two small inflatable balloons positioned on two opposite sides of the said guide, each balloon attached to one linear side of said guide, each of said balloons being connected to and communicating with a tube inside the said guide leading to a pressurized gas supply capable of feeding pressurized gas into said balloons.

7. The device of claim 6 in which the edges of the slit remote from the distal end of said endotracheal tube being spaced from one another a greater distance than the edges of the remainder of the slit and thereby defining an opening.

8. A process for introducing an endotracheal tube into a patient's trachea comprising the steps of:
   (a) inserting through the patient's mouth and pharynx a flexible guide of appropriate size to fit comfortably and of sufficient length to reach the esophagus, said guide having no more than a slight linear curvature along its length and having a male adaptor extending on the inner side of any linear curvature thereof and extending along at least a portion of the length thereof, and having a terminus, the insertion of said guide being to a position extending into the esophagus;
   (b) then fitting onto the said adaptor on said guide the endotracheal tube, the endotracheal tube comprising a flexible tube having greater linear curvature along its length than that of said guide, having a size and length appropriate for insertion through the patient's mouth and pharynx into the patient's trachea and having a distal end and a longitudinal slit starting at the distal end and extending a short distance along a portion of the length thereof, said slit being of a size to fit slidably onto the said adaptor on said guide and extending on the outer side of the linear curvature thereof, the embracing edges of the longitudinal slit being fitted onto the adaptor;
   (c) moving the distal end of said endotracheal tube into the mouth and into the pharynx, past the epiglottus and to or near the entrance to the trachea, the slit on said endotracheal tube sliding forward on the adaptor of said guide, withdrawing the said guide until the terminus of the adaptor is appropriately positioned near the dividing wall between the esophagus and the trachea, and continuing the movement of said distal end of said endotracheal tube beyond the terminus of the adaptor on said guide whereby the curvature of the said endotracheal tube causes the endotracheal tube to bend toward and into the trachea, and
   (d) thereafter advancing the said endotracheal tube into the trachea.

9. A device for facilitating the insertion of an endotracheal tube into a patient's trachea comprising:
   (a) a flexible esophageal guide having no more than slight linear curvature along its length, having size and length appropriate for insertion through the patient's mouth and pharynx and into the patient's esophagus, having an oblong cross-section and having a male adaptor having a terminus, said adaptor extending along a substantial portion of the length thereof and on the inside of any linear curvature thereof;
   (b) an endotracheal tube comprising a flexible tube having a distal end and and having greater linear curvature along its length than that of said guide, having a size and length appropriate for insertion through the patient's mouth and pharynx and into the patient's trachea and having a slit extending from the distal end thereof and over a short portion of the length thereof, said slit being of a size to fit onto the adaptor on said guide so as to be slidably mounted thereon, the said tube being connected for use by having the said slit embracing a portion of the said male adaptor.

10. The device of claim 9, in which said oblong cross-section of said guide has a bulbular portion at each end of said oblong cross-section and a smaller thickness between said bulbular portions.

11. The device of claim 8, in which the edges of the end of the slit remote from the distal end of said endotracheal tube being spaced apart from one another a greater distance than the edges of the remainder of the slit and thereby defining an opening.

12. The device of claim 11, in which the said adaptor on said guide has its terminus positioned at least a short distance from the distal end of said guide.

13. A process for introducing an endotracheal tube having a distal end and a slit therein into a patient's trachea comprising the steps of:
   (a) inserting through the patient's mouth and pharynx a flexible guide having a distal end and of appropriate cross-sectional size at least at the distal end thereof to fit comfortably inside the esophagus and of sufficient length at least to reach the esophagus, said guide having an oblong cross-section, having a slight curvature along its length and having a male adaptor having a terminus, said adaptor extending on the inner side of the linear curvature thereof and extending along at least a portion of the length thereof, the insertion of said guide being to a position where the terminus of said adaptor on said guide is at a point beyond the patient's epiglottus;
   (b) then fitting onto the said adaptor on said guide said slit, said slit running longitudinally along a short portion of the length of said endotracheal tube which has a cross-section of appropriate size and of sufficient length to reach into the trachea and having a linear curvature along its length greater than any linear curvature that the said guide may have, said slit running from the distal end of said endotracheal tube and of size and position to fit slidably onto the said adaptor on said guide and extending on the outer side of the linear curvature of said endotracheal tube; and
   (c) moving the distal end of said endotracheal tube into the mouth and into the pharynx, past the epiglottus to or near the opening of the trachea, the slit on said endotracheal tube sliding forward on the adaptor of said guide, positioning the said guide with the terminus of the adaptor appropriately positioned near the dividing wall between the esophagus and the trachea, and continuing the movement of said distal end of said endotracheal tube beyond the said terminus of the adaptor on said guide whereby the curvature of said tube causes the endotracheal tube to bend toward and into the trachea.

14. The process of claim 13, in which the distal end of said endotracheal tube is moved further and more completely into the trachea.

15. The process of claim 14, in which said guide is withdrawn, leaving the said endotracheal tube in the trachea.

16. The process of claim 13, in which said guide is withdrawn, leaving the said endotracheal tube in the trachea.

17. The process of claim 13 in which the edges of the end of the slit remote from the distal end of said endotracheal tube are spaced from one another a greater distance then the edges of the remainder of the slit and thereby define an opening.

* * * * *